United States Patent [19]

Sing

[11] 4,021,581

[45] May 3, 1977

[54] CULTURE OF SOUR DOUGH BACTERIA

[76] Inventor: Edmond L. Sing, 3860 Cheviot Place, Indianapolis, Ind. 46226

[22] Filed: Oct. 17, 1975

[21] Appl. No.: 623,449

[52] U.S. Cl. .................................. 426/61; 426/18; 426/19; 426/20; 195/48; 195/59; 195/96; 195/111
[51] Int. Cl.$^2$ ...................... C12K 3/00; A21D 8/04
[58] Field of Search ................. 195/42, 48, 59, 96; 426/18, 19, 20, 61

[56] References Cited

UNITED STATES PATENTS

| 3,592,740 | 7/1971 | Christensen | 195/59 |
|---|---|---|---|
| 3,734,743 | 5/1973 | Kline et al. | 426/18 |
| 3,891,773 | 6/1975 | Kline et al. | 426/61 |

*Primary Examiner*—Lionel M. Shapiro
*Assistant Examiner*—Robert J. Warden
*Attorney, Agent, or Firm*—Woodard, Weikart, Emhardt & Naughton

[57] ABSTRACT

A process is disclosed for rapidly and economically growing the bacterial species *Lactobacillus sanfrancisco.*

5 Claims, No Drawings

CULTURE OF SOUR DOUGH BACTERIA

BACKGROUND OF THE INVENTION

U.S. Pat. No. 3,734,743 and U.S. Pat. No. 3,891,773 summarize the extent of publicly known prior art with regard to the culture of sour dough bacteria. The disclosures of both of the above referred to patents are incorporated herein by reference. The procedures for culturing sour dough bacteria according to these prior art processes do work for growing *Lactobacillus sanfrancisco* bacteria. However, the procedures of these patents do not use inexpensive ingredients, they do not teach how to achieve high cell count in cultures and they do not provide any teachings of techniques which enable inexpensive storage of the harvested bacteria for long periods of time without loss of activity.

The present invention evolved from a prior art procedure developed by the inventor of the present invention. This prior art procedure was used commercially and because it formed the basis for the improved invention herein, is set forth in full:

PRIOR ART PROCEDURE

An aqueous solution of the following ingredients was prepared:

1.5% (solids content) of fresh yeast extractives which may be prepared according to the method of U.S. Pat. No. 3,891,773 or preferably by merely using a heat treated suspension of yeast cells in unpurified form, with the insoluble solid content allowed to settle and be removed.

5% of enzyme digested non-fat dry milk solids (enzyme digested with a protease enzyme produced by *B. subtilis* and sold under the trademark Pabst Protease L-423).

5% malt syrup extract containing 80% solids at a pH of from 6.8 to 7.

0.03% Tween 80 (sorbitan polyoxyethylene monooleate)

0.05% sodium thioglycollate.

20 parts per million of manganese in salt form.

20 parts per million of magnesium in salt form strain 114-3 of *L. sanfrancisco*.

The pH of the above mixture was maintained at 4.7 by the addition of a solution of potassium hydroxide and the temperature was maintained at 30° C. The mixture was incubated for 18 to 19 hours. When the percent transmission of light measured at 650 millimicrons reached a minimum, the fermentation was terminated and the temperature was reduced to 13° C. Minimum percent transmission over a 1 centimeter path would range from 30 to 35%. The minimum was reached for only a short time and fermentation needed to be terminated when or slightly before the minimum was reached.

Eight parts of the culture were then added to six parts of a diluent containing the following ingredients at pH 5.2:

.05% Tween 80.

2% monosodium glutamate.

9–10% glycerol the balance being reconstituted nonfat dry milk having 10.5% solids.

The resultant mixture was then cooled and stored at about −18° C. Activity at the end of one month was approximately 50% of the activity of the cells immediately after storage.

SUMMARY OF THE INVENTION

There are several aspects of the invention which are distinguishable from the prior art. One relates to the combined use of two different strains of *Lactobacillus sanfrancisco* in the growth of the organism. Another distinction relates to the use of a novel diluent which can be added to a developed culture to substantially increase shelf life of frozen cells as well as to minimize damage to cells upon freezing. A third distinction is a technique for minimizing loss of viability upon cooling to freezing temperatures which comprises cooling the mixture of culture and diluent to about 0° C. and maintaining the temperature for at least about 20 minutes and then subsequently cooling the mixture to below about −30° C. It has been found that presence of fructose in the diluent substantially improves the storage properties of the subsequently frozen mixture.

Incorporating the above distinctions from the prior art into a process for growing and storing *Lactobacillus sanfrancisco* cells provides cells of increased activity. It also substantially improves frozen storage of the bacteria at only moderately low temperature. With the procedure of the preferred embodiment of the invention, storage times of well over 6 months can be achieved while retaining high activity of the cells.

The invention provides a substantial reduction in cost of *Lactobacillus sanfrancisco*, thereby allowing commercial application of the bacteria to bread products.

DESCRIPTION OF THE PREFERRED EMBODIMENT

A process is disclosed for growing and storing bacterial species *Lactobacillus sanfrancisco* in which a culture of *Lactobacillus sanfrancisco* is incubated at about 30° C. while maintaining the pH at about 4.7 by the continuous addition of alkali. The medium contains an enzyme digested nonfat dry milk, malt syrup, and unsaturated fatty acid derivative, fresh yeast extractives and an inoculum of *Lactobacillus sanfrancisco*. After incubation for a period of time, the culture is then mixed with a diluent which includes glycerol, nonfat dry milk, a saccharide (preferably fructose but alternatively glucose or sucrose or other saccharide) and unsaturated fatty acid derivative (such as set forth in U.S. Pat. 3,891,773) and monosodium glutamate.

The mixture is then cooled preferably to a temperature of about 0° C. and maintained at that temperature for at least about 20 minutes and then subsequently cooled to below −30° C. Ideally the bacteria are then maintained at a temperature between about −30° C. and about −40° C. until just prior to the product's use.

It has been found that by the use of a combination of two different strains of *Lactobacillus sanfrancisco* produces higher activity and viability after storage. In particular, strain 114-3 and strain F-3 have been found to function extremely well in combination. These strains have been deposited in the Stock Culture Collection of the U.S. Department of Agriculture, Northern Regional Research Laboratory, Peoria, Ill. 61604, from which organization samples of these strains may be obtained. Strain 114-3 has been assigned the accession number of NRRL B-8116. Strain F-3 has been assigned the accession number NRRL B-8117.

EXAMPLE

An aqueous solution of the following ingredients was prepared:

1.75% to 2.0% (solids content) of fresh yeast extractives prepared according to the method of U.S. Pat. 3,891,773 or preferably by merely using a heat treated suspension of yeast cells in unpurified form, with the insoluble solid content allowed to settle and be removed.

5% of enzyme digested nonfat dry milk solids (enzyme digested with a protease enzyme produced by B. Subtilis and sold under the trademark Pabst Protease L-423).

5.5% malt syrup containing 80% solids at a pH of from 6.8 to 7.

0.03% Tween 80 (sorbitan polyoxyethylene monooleate)

0.05% sodium thioglycollate.

20 parts per million of manganese in salt form.

20 parts per million of magnesium in salt form.

a 50/50 blend of strain 114-3 and strain F-3 of *Lactobacillus sanfrancisco*.

The pH of the mixture was maintained at 4.7 by the addition of a solution of potassium hydroxide and the temperature was maintained at 30° C. The mixture was incubated for 17 to 18 hours. When the percent transmission of light measured at 650 millimicrons reached a minimum, the fermentation was terminated and the temperature was reduced to 5° C. Minimum percent transmission over a 1 centimeter path would range from 26 to 30%. The minimum was reached for only a short time and fermentation needed to be terminated when or slightly before the minimum was reached.

Nine parts of the culture were then added to five parts of the diluent containing the following ingredients at pH 6.5:

0.05% Tween 80
2% monosodium glutamate
9-10% glycerol
10.5-15% (preferably 12%) Iso Sweet fructose syrup (enzymatically converted corn syrup)
the balance being reconstituted nonfat dry milk having 10.5% solids.

The mixture was adjusted to pH 6.5 and was then cooled to 0° C and maintained at that temperature for 30 minutes. At the end of the 30 minute period the resultant mixture was cooled to between −30° C. and −40° C. and maintained at that temperature until use.

Activity at the end of six months was 90% of the activity of the cells immediately after storage. The above procedure produced a cell count in the final product of from $3.8 \times 10^9$ to $4.1 \times 10^9$ cells per milliliter.

In place of the fructose syrup, other saccharides may be substituted to achieve improved storage, however, it has been found that fructose is substantially more effective than other saccharides in prolonging shelf life for *L. sanfrancisco* products stored at low temperatures. The cooling of the mixture to about 0° C. prior to final cooling to the storage temperature apparently allows the cells to become acclimated to a low temperature environment and minimizes the detrimental effect which freezing otherwise would have on the cells. The presence of fructose in the final product in an amount from about 2 to 10% has been found to be very desirable.

While there have been described above the principles of this invention in connection with a specific procedure, it is to be clearly understood that this description is made only by way of example and not as a limitation of the scope of the invention.

What is claimed is:

1. A process for growing and storing the bacterial species *Lactobacillus sanfrancisco* which comprises:
   a. incubating a first mixture of
      1. enzyme digested non fat dry milk
      2. malt syrup
      3. an unsaturated fatty acid derivative
      4. fresh yeast extractives and
      5. *Lactobacillus sanfrancisco* at about 30° C while maintaining the pH at about 4.7 by the addition of alkali;
   b. after incubating, mixing about 9 parts of the first mixture with about 5 parts of a second mixture of
      1. glycerol
      2. nonfat dry milk
      3. saccharide
      4. an unsaturated fatty acid derivative and
      5. monosodium glutamate;
   c. cooling the mixture to about 0° C and then maintaining the temperature for at least about 20 minutes; and
   d. after said maintaining, cooling the mixture to below about −30° C.

2. The process of claim 1 in which after said second cooling step the temperature is maintained between about −30° C. and about −40° C, until just prior to use.

3. An improved process for growing the bacterial species *Lactobacillus sanfrancisco* which comprises the growing of both strain 114-3 and strain F-3 in combination in a suitable liquid medium for growth.

4. The process of claim 3 in which said suitable liquid medium is maintained at a temperature of about 30° C and is maintained at a pH of about 4.7 by the addition of alkali.

5. An improved process for preserving *Lactobacillus sanfranciso* cells in which a diluent carrier containing glycerol, nonfat dry milk, an unsaturated fatty acid derivative and monosodium glutamate is added to the cells prior to freezing, the improvement which comprises the additional presence of fructose in the final product in an amount from about 2 to 10%.

* * * * *